United States Patent [19]

Muriot

[11] 4,304,233
[45] Dec. 8, 1981

[54] DRAIN SPOUT CAP FOR SUCTION BAG

[75] Inventor: Edward E. Muriot, Horsham, Pa.

[73] Assignee: Health Technology Laboratories, Inc., Colmar, Pa.

[21] Appl. No.: 99,681

[22] Filed: Dec. 3, 1979

[51] Int. Cl.³ .............................................. A61J 1/00
[52] U.S. Cl. ................................... 128/272; 128/276; 215/307; 220/366
[58] Field of Search ...................... 220/366; 215/307; 128/276, 272

[56] References Cited

U.S. PATENT DOCUMENTS

| | | | |
|---|---|---|---|
| 2,070,377 | 2/1937 | Simmons | 215/307 |
| 2,655,280 | 10/1953 | Cuttell et al. | 215/307 |
| 3,963,027 | 6/1976 | Muriot | 128/276 |
| 3,982,539 | 9/1976 | Muriot | 128/276 |
| 4,004,590 | 1/1977 | Muriot | 128/276 |
| 4,135,515 | 1/1979 | Muriot | 128/276 |
| 4,192,428 | 3/1980 | Segmuller | 215/307 |
| 4,202,334 | 5/1980 | Elson | 128/272 |
| 4,206,852 | 6/1980 | Dunn et al. | 215/307 |

*Primary Examiner*—Robert W. Michell
*Assistant Examiner*—J. L. Kruter

*Attorney, Agent, or Firm*—Seidel, Gonda, Goldhammer & Panitch

[57] ABSTRACT

An improved cap is provided for selectively sealing a tube, such as a drain tube, of a suction bag used in medical/surgical suction equipment. The cap is preferably a generally hollow truncated cone, closed at one end and open at the other end to receive the tube. The inner structure of the cap generally defines two chambers. A first chamber has an inside diameter slightly larger than that of the tube. A plurality of axially oriented ribs are disposed on the inside surface of the first chamber to engage in sliding contact with the tube. A raised portion on at least one of the ribs acts as an intermediate stop which defines a first operative position of the cap. In this first operative position, air can pass through the channels defined by the inside of the first chamber wall, the ribs, and the tube. A second chamber has an inside diameter approximately equal to or slightly smaller than that of the tube. The cap is placed in a second operative position when the tube is forced beyond the intermediate stop and into the second chamber. In this second operative position, the cap acts as an air-tight seal for the tube.

12 Claims, 5 Drawing Figures

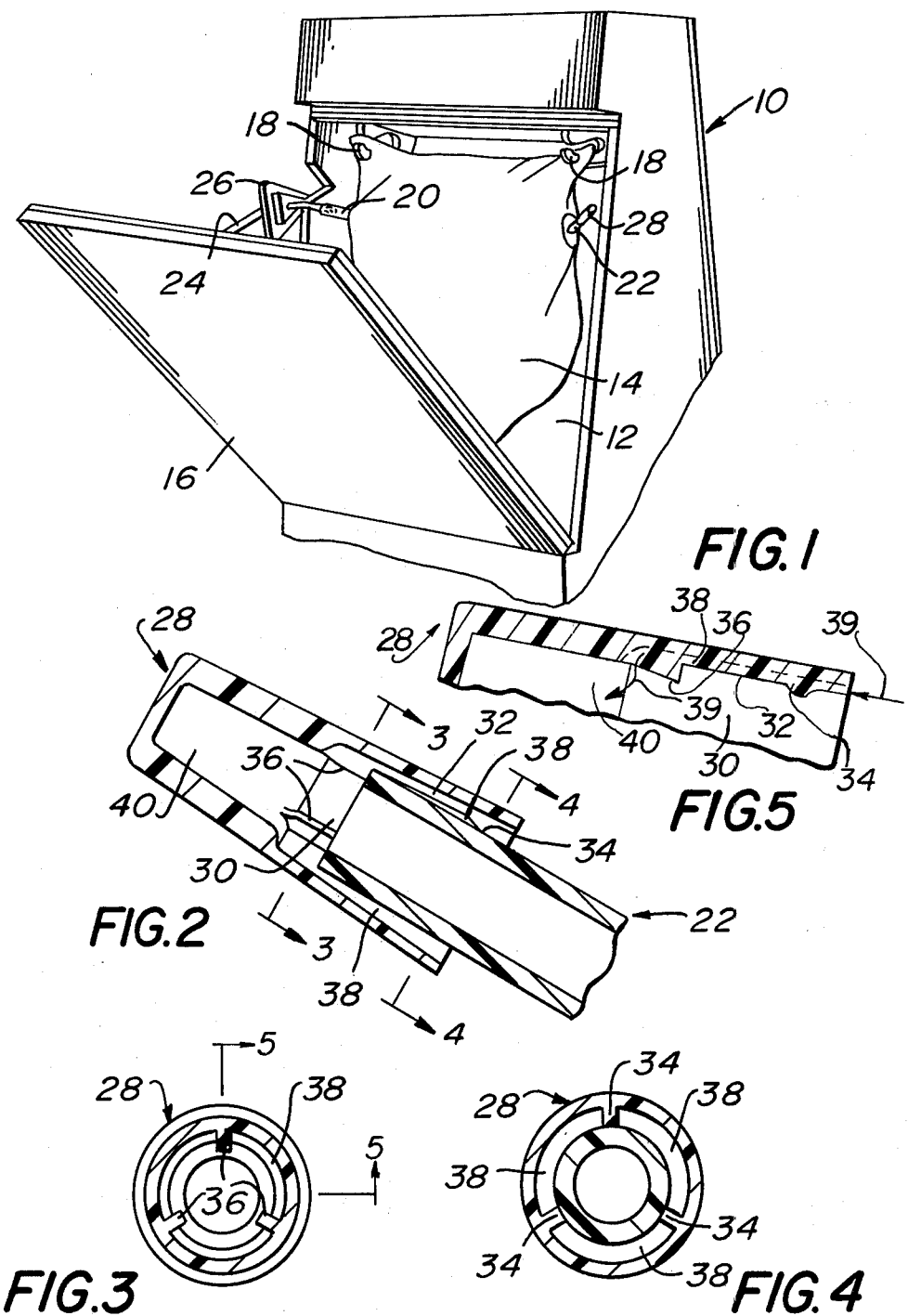

DRAIN SPOUT CAP FOR SUCTION BAG

BACKGROUND OF THE INVENTION

The present invention relates to sealing caps primarily intended for use with suction bags used in medical/surgical suction equipment to withdraw body fluids from a patient. Examples of suction equipment provided with bags of this nature are disclosed in my U.S. Pat. Nos.: 3,963,027; 3,982,539; 4,004,590; and 4,135,515. The cap described and claimed herein is an improvement over the cap disclosed in my above-identified patents.

Suction equipment of this type is characterized in that the suction bag is enclosed in a chamber. A tube leads from the patient to the bag so that body fluids withdrawn from the patient may be transferred to the bag. Air is evacuated from the chamber to produce a vacuum. The vacuum is communicated to the interior of the bag by an opening in the bag or by a tube extending from the bag within the chamber. Preferably, and as disclosed in my above-identified patents, the bag has a short tube connected to the upper portion thereof to transfer the suction from the vacuum chamber, through the bag and to the patient. This short tube can also act as a drain spout for the bag. Additionally, it is preferred to provide a cap for the drain spout in which there exists an air gap between the drain spout and the cap for the spout.

This is a significant feature in suction equipment of this type, in that an added safeguard against contamination is obtained by evacuating the air from the chamber and having the resultant vacuum communicated to the inside of the suction bag through a small air passage in a convoluted path similar to the path of a Pasteur flask. In other suction equipment, the air is evacuated directly from the suction bag, so that the suction bag and its contents are in direct communication with a suction or vacuum mechanism. This direct communication of bag and pump increases the chances of contamination in both directions, that is, from the pump through the bag and into the patient or from the contents of the bag through the pump and into the surrounding area.

Previously, another cap was used with this type of suction bag. This prior cap may best be understood by reference to FIGS. 12 and 13 of my U.S. Pat. No. 4,004,590. The drain spout of the bag in that patent is provided with a longitudinal rib, so that when the cap is applied, small air passages remain at each side of the rib. These small leakage passages provide for communication of the vacuum in the chamber to the interior of the bag. A wad of cotton or other similar material may be provided in the cap to act as a filter for contaminants. The cap is removable to permit emptying the bag through the drainage tube.

With these previous caps, the small air passages will always be open. Thus, when the bag is being transported for disposal or analysis, the contents are susceptible of dripping out through the small passage, and some communication with the surrounding atmosphere is allowed by the air passages. This shortcoming increases the possibility of contamination and complicated the task of transporting used bags.

OBJECTS OF THE INVENTION

Accordingly, it is an object of the present invention to provide an improved cap for selectively sealing a tube, such as the drain tube of a suction bag, wherein the cap allows communication of a vacuum to the interior of the bag and yet can also serve as an effective seal when desired.

Another object of the present invention to provide such an improved cap that is also simple of construction and inexpensive in manufacture, so that it is economically suitable for use with a disposable bag.

It is a further objective of the present invention to provide such an improved cap that can be changed from allowing air communication to acting as a seal by quick and uncomplicated manipulation of the cap. Other objects will become apparent after considering the following description.

SUMMARY OF THE INVENTION

A cap used to selectively seal a tube comprising: (a) a generally hollow structure having side walls connected to an end wall, the end wall defining a closed end and an opposite end defining an open end, a first chamber means defined by the interior transverse dimension of the structure at the open end, being slightly larger than the outside dimension of the tube with which the cap is adapted for use, the interior dimension of the structure reducing at some point along the axial length of the structure toward the closed end to be smaller than the outside dimension of the tube and defining a second chamber; (b) a plurality of axially oriented ribs disposed on the inside surface of the side walls and extending within the first chamber, the ribs having a portion adapted for sliding contact with the outside surface of the tube when the tube is inserted into the open end of the structure, the ribs defining passages between the ribs and between the interior surface of the side walls of the cap and the outer surface of the tube; (c) a raised portion on at least one of the ribs acting as a first position stop for the tube by abutting the end of the tube, and the raised portion having dimensions such that the tube may be forced into a second position past the raised portion and into the second chamber to form an air-tight seal for the tube.

BRIEF DESCRIPTION OF THE DRAWINGS

For the purpose of illustrating the invention, there is shown in the drawings a form which is presently preferred; it being understood, however, that this invention is not limited to the precise arrangement and instrumentalities shown.

FIG. 1 is a perspective view of a vacuum compartment of one form of medical/surgical suction equipment with the door open, illustrating a bag suspended in the compartment, the bag having a suction tube and a drain spout with the novel tube cap associated therewith.

FIG. 2 is an enlarged axial section view of the cap and drain tube.

FIG. 3 is a cross-sectional view of the cap along the lines 3—3 of FIG. 2.

FIG. 4 is a cross-sectional view of the cap and tube along the lines 4—4 of FIG. 2.

FIG. 5 is a partial cross-sectional view of the cap, but not including the tube, along the lines 5—5 of FIG. 3.

DETAILED DESCRIPTION OF THE PREFERRED EMBODIMENT

Referring to the drawings in detail, wherein like numerals indicate like elements, FIG. 1 illustrates a portion of an apparatus, designated generally at 10, for drawing liquids from body cavities. Apparatus 10 comprises primarily a vacuum chamber 12 with associated components and a suction bag 14. It will be seen that the vacuum chamber is made up of assembled flat sheets or wall elements, with the front wall 16 arranged to serve as a door or closure. In operation, front wall 16 is closed to form an air-tight seal, and air is evacuated from the enclosed chamber 12. Rather than directly connecting the bag to a source of vacuum or suction, a vacuum is created in chamber 12 which communicates with the interior of bag 14 through the spout and cap of the present invention. Means for evacuating air from chamber 12 is not depicted, and any suitable vacuum or suction arrangement may be used. A preferred means is disclosed in my U.S. Pat. Nos. 3,963,027; 3,982,539; 4,004,590; and 4,135,515, which patents also disclose the structure and operation of the apparatus. The disclosures of my U.S. Pat. Nos. 3,963,027; 3,982,539; 4,004,590; and 4,135,515 are hereby incorporated herein by reference.

Suction bag 14 is preferably detachably mounted inside vacuum chamber 12 on hook assembly 18. Bag 14 is preferably constructed so that access to the interior of bag 14 is provided by only two tubes, inlet tube 20 and drain tube 22. Inlet tube 20 is sized to receive suction tube 24. The opposite end of tube 24 is inserted into a patient's body cavity to withdraw fluids. Mounted on tube 24 is a sealing device 26 of suitable configuration to effect an air-tight seal at the point where tube 24 passes through the side wall of chamber 12. A more detailed description of preferred embodiments of sealing device 26 shown in FIG. 1 may be had by reference to my above-identified U.S. Patents.

Drain tube 22 is provided in an upper portion of the bag 14 above the normal level to which the bag 14 is filled. Tube 22 may be used for emptying the bag 14 for purposes of analysis, tests, or disposal.

However, another very important function is provided by drain tube 22. As mentioned above, vacuum is created by evacuating air directly from vacuum chamber 12. Suction tube 24, however, comminicates only with the interior of suction bag 14 through inlet tube 20. To allow the vacuum created in chamber 12 to draw body fluids through suction tube 24, the vacuum must be communicated to the interior of suction bag 14. Drain tube 22 provides an opening from bag 14 to chamber 12 whereby the pressure is equalized between the bag 14 and the chamber 12.

A cap 28 is provided for tube 22. The cap 28 provides a seal that closes drain tube 22 when the bag 14 is being transported or stored. The seal is an important protection against contamination, either from the contents of the bag to the surrounding areas or from the surrounding atmosphere to the contents of the bag which might prevent a true analysis of the bag contents. The cap prohibits spills and also provides an air-tight seal.

It is desirable that the cap 28 be left in place on tube 22 even while the bag 14 is being used inside suction chamber 12. Equalization of pressure between chamber 12 and bag 14 is provided by small air passages between cap 28 and drain tube 22. This was accomplished in the previous drain tube and cap as shown, for example, in U.S. Pat. No. 4,004,590, FIGS. 12 and 13, by providing a single axial rib on the drain tube. The inside diameter of the cap was larger than the outside diameter of the drain tube, being approximately equal to the outside diameter of the drain tube plus the height of the rib. Thus, small air passages were formed on either side of the rib between the air tube and the inside wall of the cap. However, in this prior tube and cap arrangement the small air passages remained open even while the bag was being transported for disposal or analysis.

The improved cap 28 of the present invention has two operational positions when used with tube 22. In the first position, small air passages exist between cap 28 and tube 22. In the second position, cap 28 forms an air-tight seal over tube 22.

Referring now to FIG. 2, it may be seen that cap 28 is a generally truncated cone having slightly tapering side walls, closed at one end, and open at the other to receive the end of tube 22. The cap may be of other shapes so long as the interior structure is as described hereinafter. Cap 28 has two interior chambers. A first chamber 30 begins at the open end of cap 28. The small inside diameter of chamber 30 is slightly larger than that of the outside diameter of tube 22. Extending within chamber 30 from the inside wall of chamber 30 are axially oriented ribs 32. In the embodiment shown, each of the ribs 32 has a raised fin 34 near the inlet opening of cap 28.

The effective inside diameter of cap 28 (measured by considering the interior portions of fins 34 as defining points of a generally circular shaped interior portion of the cap) is approximately equal to the outside diameter of tube 22, so that when tube 22 is inserted into the open end of cap 28, there is a sliding engagement between tube 22 and fins 34. At least one and preferably each rib 32 has another raised portion 36 on its end remote from fin 34. The raised portions 36 act as an intermediate stop when the cap 28 is placed over tube 22. This intermediate stop defines a first operative position of cap 28 on tube 22. In this first operative position, there are small air passages 38 between the tube 22 and the inside wall of cap 28 which allows equalization of pressure between the vacuum chamber 12 and the bag 14.

FIG. 5 is a partial sectional view of cap 28 taken along lines 5—5 of FIG. 3. FIG. 5 illustrates in phantom the air passage 38 between the ribs 32. Arrow 39 illustrates the flow of air through air passage 38 which is operative when the end of tube 22 abuts the raised portions 36 of ribs 32.

The raised portions 36 are not so large as to provide an impassable stop for the end of tube 22, but rather are small enough so that when sufficient force is applied to cap 28, tube 22 will be forced past the raised portions 36. Once past raised portion 36, the end of tube 22 can pass into the second chamber 40.

Chamber 40 has an inside diameter approximately equal to or slightly smaller than the outside diameter of tube 22. Thus, when the end of tube 22 is inserted into chamber 40, an air-tight seal is formed. This is the second operative position of cap 22.

Although the cap is illustrated in FIGS. 3 and 4 in its preferred embodiment as being generally circular in transverse cross section, the cap may have any shape as long as its internal shape matches the external shape of the tube or drain spout over which it fits. Preferably, the cap is made of a material which is capable of being slightly deformed, such as a yieldable polymeric material. This is a factor since tube 22 must be able to be forced past raised portion 36 of ribs 32 into chamber 40. The presently preferred materials are polyvinylchloride and polyethylene, but other materials which can yield may also be used.

It is also important that the cap be made of a yieldable material if it is intended for use with a drain tube made of a rigid non-yielding material. If this were the case, the raised portions 36 and the side walls of the cap would have to yield to allow the end of drain tube 22 to be sealed by the walls of chamber 40.

As illustrated in FIGS. 2, 3 and 4, cap 28 preferably is a one-piece integral structure. Thus, the end wall is integrally formed with the side walls and the ribs 32 are integrally formed with the inner surface of the side walls. Because of this structure, the cap may be efficiently and economically formed by molding processes well known to those of ordinary skill in the art of molding.

In operation then, bag 14 is hung inside vacuum chamber 12 on hook assembly 18. Suction tube 24 is inserted into inlet tube 20. Cap 28 is pushed onto drain tube 22 until the stops provided by raised portion 36 are encountered. Then front wall 16 is closed, sealing the vacuum chamber. Air is evacuated from the chamber 12. The resulting vacuum is communicated to the interior of bag 14 through the small air passages 38 between cap 28 and drain tube 22. This vacuum provides suction through suction tube 24 to drain body fluids from the patient.

When the drainage operation is terminated, or the bag is filled, the evacuation of air from chamber 12 may be stopped and chamber 12 opened to remove bag 14. When bag 14 is removed, cap 28 is pushed into its second operative position on tube 22. In this position, the cap 28 is forced past the stops or raised portions 36 and the end of tube 22 enters the second chamber 40 where an air-tight seal is effected. Suction tube 24 is then removed from inlet tube 20 and is sealed in any suitable fashion, as by means of a plain sealing cap. Bag 14 is thus sealed for transportation, for disposal or analysis.

The present invention may be embodied in other specific forms without departing from the spirit or essential attributes thereof and, accordingly, reference should be made to the appended claims, rather than to the foregoing specification, as indicating the scope of the invention.

I claim:

1. A cap used to selectively seal a tube comprising:
    (a) a generally hollow structure having side walls connected to an end wall, the end wall defining a closed end and an opposite end defining an open end, a first chamber defined by the interior dimension transverse to the longitudinal axis of the structure at the open end being larger than the outside dimension of the tube with which the cap is adapted for use, a second chamber adjacent the closed end of the structure having a dimension transverse to the longitudinal axis of the structure smaller than the outside dimension of the tube and defining thereby a second chamber;
    (b) a plurality of axially oriented ribs disposed on the inside surface of the side walls and extending within the first chamber, the ribs having a portion adapted for sliding contact with the outside surface of the tube when the tube is inserted into the open end of the structure, air passages between the ribs and the interior surface of the side walls of the structure and the outer surface of the tube; and
    (c) means on at least one of the ribs acting as a stop for the tube in a first position whereby the tube is not sealed by the cap by abutting the end of the tube, the means having dimensions such that the tube may be forced into a second position past the means and into the second chamber to form an air-tight seal for the tube.

2. A cap as in claim 1 wherein each of the ribs contains the means.

3. A cap as in claim 1 wherein the cap is generally circular in transverse cross-section.

4. A cap as in claim 1 wherein the cap has a shape of a truncated cone with the closed end having a smaller transverse diameter than the open end.

5. A cap as in claim 1 wherein the portion of the rib adapted for sliding contact with the tube is a raised portion adjacent to the open end of the structure.

6. A cap as in claim 1 made of a yieldable material.

7. A cap as in claim 1 made of a yieldable polymeric material.

8. A cap as in claim 1 wherein the ribs are integrally formed with the side walls.

9. A cap as in claim 1 wherein the end wall is integrally formed with the side walls.

10. A cap as in claim 1 wherein the means acting as a stop for the tube in a first position is a second raised portion of the rib which extends radially inwardly within the structure.

11. A cap as in claim 10 wherein the second raised portion is located on the rib at a location closer to the second chamber than to the open end of the structure.

12. A cap as in claim 1 wherein a shoulder defines the opening of the second chamber where it meets the first chamber.

* * * * *